US00PP11331P

United States Patent [19]

Plevier

[11] Patent Number: Plant 11,331

[45] Date of Patent: Apr. 4, 2000

[54] ALSTROEMERIA PLANT NAMED 'VIRGINIA'

[75] Inventor: F. B. Plevier, Sassenheim, Netherlands

[73] Assignee: Koninklijke Van Zanten B.V., Hillegom, Netherlands

[21] Appl. No.: 09/106,647

[22] Filed: Jun. 29, 1998

[51] Int. Cl.[7] ..... A01H 5/00

[52] U.S. Cl. ..... Plt./309

[58] Field of Search ..... Plt./309

[56] References Cited

PUBLICATIONS

UPOV–ROM, 1999/02, Plant Variety Database, GTI Jouve Retrieval Software, 2 citations for 'Virginia', 1 citation for 'My Virginia'.

*Primary Examiner*—Howard J. Locker
*Attorney, Agent, or Firm*—Christie, Parker & Hale, LLP

[57] ABSTRACT

A new and distinct variety of Alstroemeria plant producing flowers of good quality and attractive white coloration.

1 Drawing Sheet

BACKGROUND OF THE INVENTION

The present invention relates to a new and distinct variety of Alstroemeria which is a cross of two unnamed, undistributed seedlings. The varietal denomination of the new variety is 'Virginia'.

The first act of asexual reproduction of 'Virginia' was in Rijsenhout, The Netherlands, by micropropagation (tissue culture). Asexual reproduction by tissue culture through successive generations in Rijsenhout, The Netherlands, has demonstrated that the combination of characteristics as herein disclosed for 'Virginia' are firmly fixed and retained through successive generations.

SUMMARY OF THE INVENTION

The new variety of Alstroemeria, 'Virginia', produces strong, thick stems and about 5 to 8 peduncles per stem.

DESCRIPTION OF ILLUSTRATION

The new variety of Alstroemeria hybrid is illustrated in the accompanying illustration, which shows typical flower and stem characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Rijsenhout, The Netherlands in the month of April. Color designations indicated are in accordance with The Royal Horticultural Society Colour Chart by color plate designations.

'Virginia' has not been observed under all possible environmental conditions. Phenotypic expression may vary with variations in environment such as temperature, light intensity, day length and growing and cultural conditions.

Botanical classification:
- *Family*.—Amaryllidaceae.
- *Genus*.—Alstroemeria sp.
- *Commerical*.—Alstroemeria hybrid.

Origin: Seedling.

Plant:
- *Form*.—Upright.
- *Height*.—About 120 to 200 cm.
- *Flower stem*.—Length: About 100 to 200 cm. Color: Near 144A. Quantity of leaves: About 20 to 40 leaves per stem. Size of leaf: About 15 to 18 cm long and about 1 to 3 cm wide. Shape of leaf: Lanceolate. Margin: Minutely crimped. Texture: Upper side leathery. Leaf Color: Upper side near 137A; underside near 137C. Venation: Linear.
- *Rhizomes*.—About 10–30 cm, near 155D.
- *Peduncle*.—Length: About 10–15 cm. Color: Near 144A. Aspect: Erect.

Bud stage:
- *Form*.—Oval.
- *Size*.—Length about 3 to 4 cm; diameter about 1½ cm.
- *Opening buds*.—Buds open from the lowermost to the top.
- *Color of tepals when tepals begin to unfurl*.—White/greenish.

Flower stage:
- *Blooming habit*.—Continuous.
- *Time of flowering*.—Year-round.
- *Flower*.—Size: Medium. Diameter: About 6 to 7 cm. Depth: About 5 to 6 cm. Borne: Cluster, about 2–8 blooms per umbel. Shape: Cup shape. Color: Near 155D. Strength: Strong. Discoloration after full bloom: Weak/absent.
- *Bloom*.—Form: Open/tubular. Tepalage: 6. Shape of tepals: 3 obovate, 3 lanceolate. Margin of tepals: Minutely crimped. Texture of tepals: Smooth. Persistence: Flowers fall off after maturity. Lasting quality: On plant about 3 weeks, as a cut flower about 14–16 days.
- *Color*.—Near 155D on both inner and outer tepals. Inner tepals: Two inner lateral tepals have about 20–40 spots, near 59A, inner median tepal has no spots, color of tepals when tepals first divide and begin to unfurl, near 155A. Outer tepals: White with a bit of green near 135D at the tip. Discoloration as bloom ages: When bloom opens the color is creme/white and becomes clear white.
- *Fragrance*.—Absent.

Reproductive organs:
- *Stamens*.—Near 146B and 155D.
- *Anthers*.—White.
- *Filaments*.—About 3 to 4 cm, near 155D.

*Pollen*.—Grey/green, not fertile.
*Pistils*.—1. Styles: About 3 to 4 near 155D. Stigmas: White.
*Shape of fruit*.—Ovoid. Size: About 0.5 to 1 cm long.

I claim:

1. A new variety of Alstroemeria plant substantially as herein shown and described.

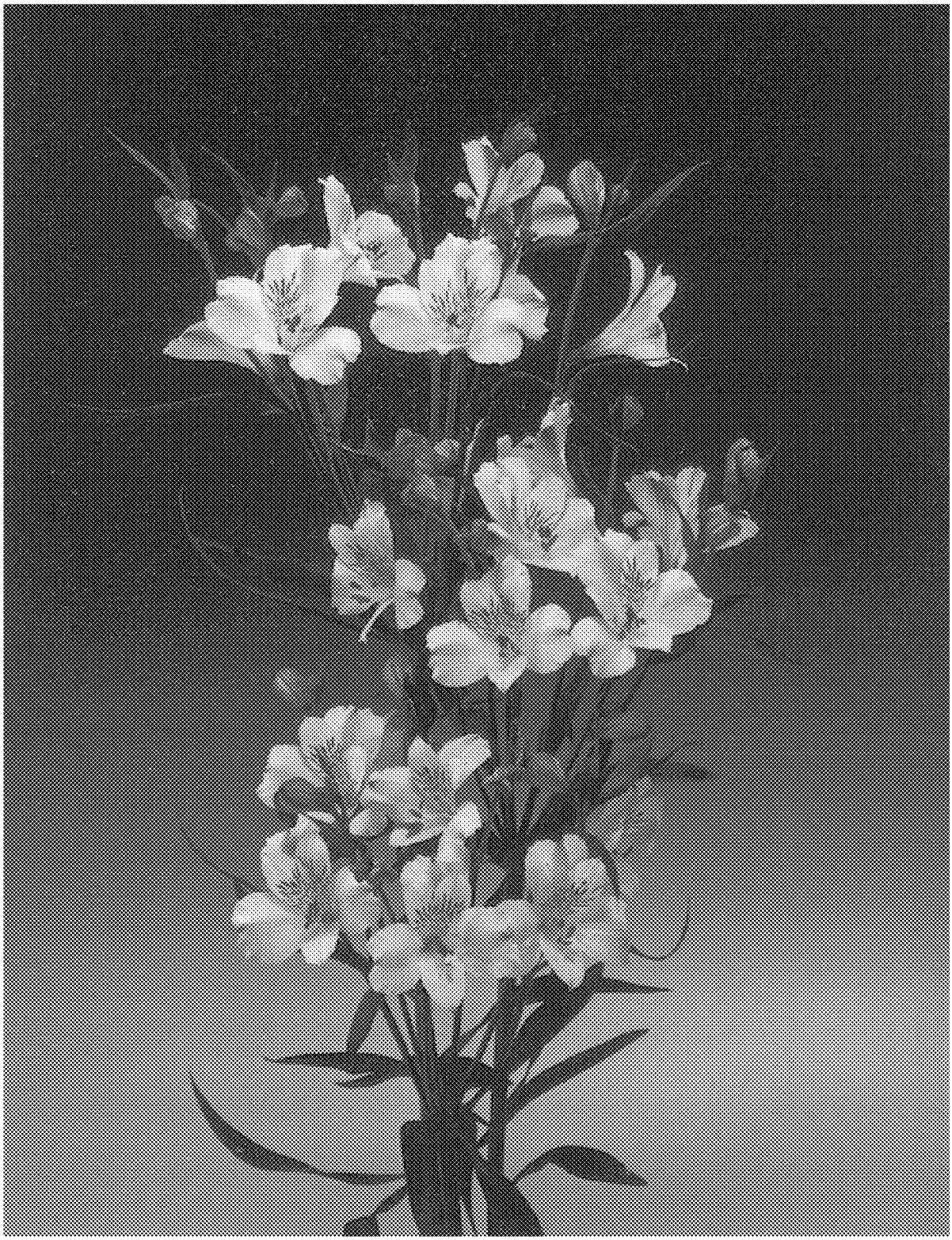

* * * * *